US009023403B2

(12) United States Patent
Pecher et al.

(10) Patent No.: US 9,023,403 B2
(45) Date of Patent: May 5, 2015

(54) **USE OF A *LEPECHINIA CAULESCENS* EXTRACT AS A COSMETIC AGENT, AND COSMETIC COMPOSITION CONTAINING SAME**

(75) Inventors: Virginie Pecher, La Chapelle Saint Mesmin (FR); Virginie Leplanquais, Fay-aux-Loges (FR); Krystell Lazou, Orléans (FR); Marc C M Dumas, Saint Jean le Blanc (FR)

(73) Assignee: LVMH Recherche, Saint Jean De Braye (FR)

( * ) Notice: Subject to any disclaimer, the term of this patent is extended or adjusted under 35 U.S.C. 154(b) by 240 days.

(21) Appl. No.: 12/477,433

(22) Filed: Jun. 3, 2009

(65) Prior Publication Data

US 2009/0304829 A1 Dec. 10, 2009

(30) Foreign Application Priority Data

Jun. 6, 2008 (FR) ...................... 08 53795

(51) Int. Cl.
*A61K 36/00* (2006.01)
*A61K 8/00* (2006.01)
*A61K 8/06* (2006.01)
*A61K 8/97* (2006.01)
*A61K 36/53* (2006.01)
*A61Q 3/00* (2006.01)
*A61Q 7/00* (2006.01)
*A61Q 19/08* (2006.01)

(52) U.S. Cl.
CPC . *A61K 8/97* (2013.01); *A61K 36/53* (2013.01); *A61Q 3/00* (2013.01); *A61Q 7/00* (2013.01); *A61Q 19/08* (2013.01)

(58) Field of Classification Search
USPC ................... 424/725, 401
See application file for complete search history.

(56) References Cited

U.S. PATENT DOCUMENTS

| 4,089,942 | A | * | 5/1978 | Bore et al. ....................... 424/47 |
| 4,911,931 | A | * | 3/1990 | Baylink ........................ 424/606 |
| 6,124,362 | A | | 9/2000 | Bradbury et al. |
| 6,265,370 | B1 | | 7/2001 | Newbegin |
| 2003/0130356 | A1 | * | 7/2003 | Frydman et al. ............... 514/667 |
| 2006/0216255 | A1 | * | 9/2006 | Lee et al. ...................... 424/70.1 |
| 2007/0259057 | A1 | * | 11/2007 | Sugita et al. ................... 424/756 |

FOREIGN PATENT DOCUMENTS

| DE | 10308852 | * | 2/2003 |
| WO | 2006069192 A1 | | 6/2006 |

OTHER PUBLICATIONS

What are the Topical Uses for DMSO? Oct 11, 2009. Retrieved from the internet. <http://www.ehow.com/facts_5516388_topical-uses-dmso.html>. Retrieved on Nov. 17, 2010. 1 page.*
Estrada-Soto. Spasmolytic Action of *Lepechinia caulescens* is Through Calcium Channel Blockage and NO Release. Journal of Ehtnopharmacology. 114. 2007. pp. 364-370.*
Balch. Prescription for Nutritional Healing. Penguin. 2006. p. 274.*
Rodriguez-Lopez et al. Spasmolytic Activity of Several Extracts Obtained From Some Medicinal Plants. Fitoerapia. 74 (2003) 725-728.*
Viable-herbal.com. Retrieved from the internet. <http://web.archive.org/web/20000124113842/http://viable-herbal.com/herbology1/herbs42.htm>. Web archive date Jan. 12, 2000. Retrieved on Nov. 18, 2010. pp. 1-4.*
Rojas et al. Antimicrobial Activity of Selected Peruvian Medicinal Plants. Journal of Ethnopharmacology. 88. 2003. pp. 199-204.*
http://replay.waybackmachine.org/20020301012412/http://earthnotes.tripod.com/howtoextracts.htm.*
amazon.com. Retrieved from the internet. Retrieved on Nov. 10, 2011. <http://www.amazon.com/Ambiance-Cosmetics-Volumizing-Applicator-Brunette/dp/B005HJ3GMS>. 3 pages.*
Fraise et al. Russell, Hugo & Ayliffe's Principles and Practice of Disinfection, Preservation & Sterilization. John Wiley and Sons. 2008. p. 54.*
Chu et al. Study on Extraction Efficiency of Natural Antioxidant in Coffee by Capillary Electrophoresis With Amperometric Detection; Eur. Food Res. Technol (Published Online Jun. 2007).*
Parejo et al. Investigation of *Lepechinia graveolens* for Its Antioxidant Activity and Phenolic Composition; Journal of Ethnopharmacology; 94 (2004) 175-184.*
Parzaile, E., Cookbook Herbalism Basic Principals & Skills-Traditional Systems; Online, URL < http://earthnotes.tripod.com/basics.htm> accessed online Jan. 21, 2014, archived to Aug. 20, 2006 with Archive.org (www.archive.org) 9 pages.*
Torres, in Healing With Herbs and Rituals: A Mexican Tradition; University of New Mexico Press; USA (2006), pp. 86, 88, 89, 91, 92 and 93.*
Wikipedia; Dimethyl Sulfoxide; Online, URLhttp://en.wikipedia.org/wiki/Dimethyl_sulfoxide accessed Jan. 20, 2014, 8 pages.*
Wikipedia; Glycerol; Online, URL< http://en.wikipedia.org/wiki/Glycerol> accessed Jan. 20, 2014, archived to Oct. 11, 2007.*
Deveraux et al.; IAP Family proteins—suppressors of apoptosis; Genes & Development; 13 (1999), pp. 239-252.

(Continued)

*Primary Examiner* — Patricia Leith
(74) *Attorney, Agent, or Firm* — Baker & Hostetler LLP

(57) ABSTRACT

The invention relates to the use of a plant extract of a plant belonging to the *Lepechinia* genus, in particular an extract of the plant species *Lepechinia caulescens*, as a cosmetic agent or as an active agent in cosmetic compositions.

36 Claims, No Drawings

(56) References Cited

OTHER PUBLICATIONS

Xie et al.; A study of using tissue-engineered skin reconstructed by candidate epidermal stem cells to cover the nude mice with full-thickness skin defect; Journal of Plastic, Reconstructive & Aesthetic Surgery; 2007, 60(9):983-990.

Marconi et al.; Survivin Identifies Keratinocyte Stem Cells and is Downregulated by Anti-Beta1 Integrin During Anoikis; Stem cells 2007, 25:149-155.

Grossman et al.; Transgenic expression of survivin in keratinocytes counteracts UVB-induced apoptosis and cooperates with loss of p53; Journal of Clinical Investigation; 2001, 108:991-999.

Jones et al.; Separation of Human Epidermal Stem Cells from Transit Amplifying Cells on the Basis of Differences in Integrin Function and Expression; Cell 1993, vol. 73, pp. 713-724.

Varlet et al.; Age-Related Functional and Structural Changes in Human Dermo-Epidermal Junction Components; Journal Investigative Dermatology;symp Proc; 1998, 3:172-179.

Bosset et al.; Decreased expression of keratinocyte Beta1 integrins in chronically sun-exposed skin in vivo; British Journal of Dermatology 2003, 148:7770-7778.

Zuliani et al.; Apoptosis and Proliferation during Human Epidermal Aging after an Acute UV Exposure: and in vivo Immunohistological Study; J Invest Dermatology 2004, 123:2, A50, 302.

Vader et al; Surivivin mediates targeting of the chromosomal passenger complex to the centromere and midbody; EMBO Reports, 2006, 7, 1, pp. 85-92.

Delgado et al., Di- and Triterpenoid Acids from *Lepechinia caulescens*; Phytochemistry, 1994, 37 (4), 1119-21).

Rodriguez-Lopez et al., Spasmolytic activity of several extracts obtained from some Mexican medicinal plants; Fitoterapia, 2003 74 725-728.

Ramos et al, Hypoglycemic Activity of Some Antidiabetic Plants; Archives of Medical Research (Mex.), 1992 ; 23 105.

Snyder, L.R.; Classification of the solvent properties of common liquids; Journal of Chromatography, 92(1974), pp. 223-230.

* cited by examiner

USE OF A *LEPECHINIA CAULESCENS* EXTRACT AS A COSMETIC AGENT, AND COSMETIC COMPOSITION CONTAINING SAME

CROSS-REFERENCE TO RELATED APPLICATIONS

This application claims the benefit of French Application No. 0853795, filed Jun. 6, 2008, the entirety of which is incorporated herein.

TECHNICAL FIELD

The present invention relates to the use of an extract of plants belonging to the *Lepechinia* genus as a cosmetic agent and to a cosmetic composition containing same. More particularly, the subject of the invention is the use of an extract of the plant species *Lepechinia caulescens* as a cosmetic agent, as an active agent in cosmetic compositions, and also the cosmetic care methods using said compositions.

BACKGROUND

Apoptosis is an active biological process of elimination, by fragmentation, of certain cells of the organism.

It constitutes a programmed elimination of cells at the biological tissue level, under genetic control. The elimination may be natural (surplus cells in the tissue) or induced by various forms of stress.

The biological cascade of apoptosis is known and uses a number of effectors such as caspases, in particular the effector caspases 3 or 7, which will implement the apoptosis programme, and the initiating caspases 8 and/or 9, which will trigger it.

A certain number of apoptosis inhibitors are also known (Deveraux et al., *Genes Dev.* 13 (1999), pp. 239-252), among which is survivin. These inhibitors therefore regulate cell survival, thus participating in cell homeostatis in biological tissues.

Survivin, the only member of the IAP (Inhibitor of Apoptosis Protein) family, is a bifunctional protein capable both of balancing the apoptosis of cells and of regulating the cell cycle thereof.

Survivin inhibits in particular the activation of certain caspases, in particular caspases 3, 7 and 9.

This protein is expressed in strongly growing embryonic tissues, but is not expressed in adult differentiated tissues, except in tissues that have a physiological cell renewal and/or are involved in a repair process. Thus, at the cutaneous level, it is most particularly expressed in the keratinocytes of the basal layer of the epidermis, which provide formation and renewal of the latter.

It is in this basal layer that the epidermal stem keratinocytes are found, these being cells with a high potential for regeneration of this tissue, which have been demonstrated to be the most effective in forming a complete epidermis (J L Xie et al., *J Plast Reconstr. Aesthet. Surg.* 2007; 60(9); 983-90).

Now, it has been shown that survivin is mainly expressed in the stem cells of the epidermis (Marconi A, Dallaglio K, Lotti R, Vaschieri C, Truzzi F, Fantini F, Pincelli C, Stem cells 2007: 25: 149-155).

Conversely, overexpression of survivin shows a significant decrease in the number of apoptotic cells in the epidermis after exposure to ultraviolet radiation (Grossman et al., 2001 J Clin Invest 108; 991-999).

It has also been demonstrated that the inactivation of beta-1 integrins completely abolishes the cellular expression of survivin (Marconi A et al., Stem cells 2007: 25: 149-155) and leads the cells to apoptosis.

Beta-1 integrins are adhesion proteins through which the keratinocytes of the epidermal basal layer adhere to the proteins of the dermal-epidermal junction.

Beta-1 integrins are expressed more strongly by the stem cells of the epidermis (P. Jones, *Cell* 1993, 73: 713-724, Kaur *J Invest Dermatol* 2006, 126, 1450-1458), which corroborates the observation of a stronger expression of survivin in these cells.

Now, during ageing, a drop in the expression of beta-1 integrins in the keratinocytes (B Le Varlet et al. *J Investig Dermatol Symp Proc.* 1998, 3; 172-179) and in the wrinkled skin areas exposed to light (S Bosset et al. *British J Dermatol* 2003, 148; 7770-778) is observed.

Thus, the proteins which ensure maintenance of survivin in the basal cells of the epidermis decrease with age, and, in parallel, an increase in the sensitivity of the cells to apoptosis and a decrease in cycling cells are observed (Zuliani et al., *J. Invest. Dermatol.* 2004, 123:2, A50, 302), these observations converging to indicate a probable survivin deficiency in ageing skin.

In addition to its apoptosis-regulating role, survivin has been identified as a constituent of the "chromosomal passenger complex" which coordinates the chromosomes with the cytoskeleton during mitosis (Vader et al., EMBO reports, 2006, 7, 1, 85-92); it therefore plays an essential role in normal cell division, this division being impaired during ageing with, as a consequence, less renewal of the epidermis, thinning thereof, and the development of wrinkles.

Survivin is therefore a regulator of the survival and of the resistance of keratinocytes; it acts by modulating the sensitivity of apoptosis of the keratinocytes located in the basal layer of the epidermis, including the stem cells. It also regulates their capacity for renewal and for regeneration of the epidermis.

It thus makes it possible to spare the cell stock of the epidermis and to maintain efficient epidermal cell renewal.

Document WO 2006/069192 (GILLETTE Co) discloses the use, in cosmetics, of survivin-inhibiting agents for a hair and body-hair growth reduction effect.

To date, no compounds that act as survivin-expression stimulators have been described for uses in cosmetics.

As regards the plant of the *Lepechinia* genus, said genus comprises approximately 40 species, among which is *Lepechinia caulescens*, which are essentially found in Mexico and South America.

*Lepechinia caulescens* (Syn: *Horminum caulescens* Ortega), one of these species, is an erect perennial low plant 30 to 80 cm in height, the vegetative cycle of which is seasonally dependent, and which is found in Mexico, Nicaragua and Guatemala at altitudes between 1200 and 3900 m. *Lepechinia caulescens* is a species recognized in traditional medicine, in particular for its activity on diarrhoea and vomiting.

Published data exist on studies aimed at isolating chemical compounds present in these plants.

Di- and triterpenoid acids have been isolated from above-ground parts of *Lepechinia caulescens* (Delgado et al., *Phytochemistry*, 1994, 37 (4), 1119-21).

Some authors have demonstrated the vasorelaxing activity of a methanolic extract of *Lepechinia caulescens*, said activity being mediated by the presence of oleanolic acid and ursolic acid, which are two triterpenoic acids isolated from this plant.

Other authors have demonstrated, on an ileum isolated from rat, the spasmolytic activity of an organic extract obtained from the whole plant of the species *Lepechinia caulescens*, confirming experimentally the traditional use of the plant by local Mexican populations (Rodriguez-Lopez et al., *Fitoterapia*, 2003 74 725-728).

Some authors have also characterized an insulinomimetic activity of an organic extract of this plant (Roman et al, *Arch. Med. Res. (Mex.)*, 1992; 23 105).

More recently, document U.S. Pat. No. 6,265,370 has described the use of fresh or dried flowers of *Lepechinia* in pulverized form, as a scented agent in a method for making soap.

However, to date, no data exist concerning the use of a plant species of the *Lepechinia* genus, in the form of the product of any method of extraction, as an active agent in cosmetic compositions.

SUMMARY

The present invention is direct to cosmetic compositions at least one cosmetic agent comprising a plant extract obtained from a plant material formed by, or comprising, at least one plant of which the species belongs to the *Lepechinia* genus, wherein the extract is obtained by bringing the plant material into contact with a polar solvent that is a $C_1$-$C_4$ alcohol or a mixture of a $C_1$-$C_4$ alcohol and water, said extract being admixed with a cosmetically acceptable carrier compatible with topical application to a body zone. Methods of using these cosmetically acceptable agents is also described.

DETAILED DESCRIPTION OF ILLUSTRATIVE EMBODIMENTS

Over the course of their studies, the inventors of the present invention have demonstrated that an extract obtained from a plant material comprising or formed from at least one plant of the *Lepechinia* genus, in particular of the plant species *Lepechinia caulescens*, activates or stimulates the expression of the survivin protein in the keratinocytes of the basal layer of the epidermis, and more particularly in the stem cells of said basal layer.

Said extract thus plays a protective role with respect to the regenerative cells of the human epidermis, and most particularly the stem cells of the basal layer of the epidermis.

These extracts can thus be used as a cosmetic or dermatological agent, or as an active agent in cosmetic or dermatological compositions, aimed in particular at preventing or delaying the appearance of the signs of skin ageing or reducing the effects thereof, or else at promoting cell or tissue longevity; at promoting the reconstruction of a damaged epidermis and also the healing of cutaneous wounds in normal skin and ulcerative wounds that heal poorly; at promoting hair regrowth or hair reinforcement; at promoting the growth of the nails and/or reinforcing the strength thereof, as an adjuvant for prolonging cell cultures in vitro for the purposes of cultured epidermis production (reconstructed epidermis) for therapeutic purposes, for example in grafts or else in maintaining purified populations of stem cells of the epidermis or hair follicles in vitro for therapeutic or research purposes.

The principal purpose of the invention is to propose the use of a cosmetically acceptable plant extract obtained from plants, as a cosmetic agent.

Another purpose of the invention is the use of said extract as a cosmetic agent, or as an active agent in cosmetic compositions, and the cosmetic care methods using said compositions:

a) for preventing or delaying the appearance of the signs of skin ageing or slowing down the effects thereof, and/or b) for reconstructing the epidermis or the stratum corneum thereof, when it is damaged, in particular by ultraviolet radiation, and/or c) for restoring the functioning of the hair cycle, in order to prevent or slow down hair loss, to accelerate or promote hair regrowth, for example in the case of alopecia, or to reinforce brittle hair, and/or d) for promoting growth of the nail and/or reinforcing the strength thereof.

Another main purpose of the invention is to provide a cosmetic care method, using a cosmetically acceptable plant extract, in particular for carrying out the types of cosmetic care indicated above.

A further main purpose of the invention is to provide a method for the in vitro culture of stem cells and/or of cells with a high clonogenic potential for the purposes of fundamental studies or of production of cultured epidermis, such as reconstructed epidermis, for therapeutic purposes, for example, as in the case of a graft, following burns or ulcerative wounds which heal poorly, comprising the use of a plant extract that is acceptable with said cell culture, obtained from plants.

A first aspect of the present invention relates to the use, as a cosmetic agent, of a plant extract obtained from a plant material formed by, or comprising, at least one plant of which the species belongs to the *Lepechinia* genus, said extract is obtained by bringing the plant material into contact with a polar solvent selected from a $C_1$-$C_4$ alcohol and a mixture of said alcohol with water.

The plant material used may be the whole plant or a part of the plant, such as the root, the rhizome or an above-ground part, in particular the stem, the leaves, the flowers, the seeds or the floral buds.

The extract is preferably obtained from the above-ground parts of the plant, and in particular the leaves.

Prior to the extraction step itself, the plant material may have been dried and/or ground.

According to one preferred embodiment of the extraction, the plant material is in the dry and ground state.

In addition to the plants of the *Lepechinia* genus, and in particular of the plant species *Lepechinia caulescens*, the plant material from which the extract of the invention is prepared may comprise one or more other plants, without distinction in the form of whole plants or of parts of a plant.

These plants may be of a genus other than the *Lepechinia* genus, or plants of another family, known to have properties similar or complementary to those demonstrated for the plants of the *Lepechinia caulescens* genus.

Plants of which the extracts are known to slow down or prevent the effects of skin ageing, by various mechanisms, such as maintaining the integrity of the skin structure or an action on wrinkles, may in particular be chosen.

The extract may be prepared by various extraction methods known to those skilled in the art.

However, the extraction is carried out by bringing the selected plant material into contact with a polar solvent or a mixture of polar solvents selected from a $C_1$-$C_4$ alcohol or a mixture of polar solvent selected from a $C_1$-$C_4$ alcohol and water.

According to the present invention, the expression "polar solvent" signifies that the solvent has a polarity index value P' which is greater than or equal to a value of 4.

The polarity index is a value calculated on the basis of thermodynamic values (of solubility and of change of state) which demonstrates the more or less polar nature of a molecule.

For the polarity indices of the solvents, reference will be made to the article by L. R. SNYDER; Classification of the solvent properties of common liquids; *Journal of Chromatography*, 92 (1974), 223-230, which is included in the present application by way of reference.

As polar solvent or mixture of polar solvents that can be used for the extraction step, said $C_1$-$C_4$ alcohol is selected from ethanol or butanol, a glycol preferably chosen from glycerol, butylene glycol and propylene glycol, and mixtures thereof.

The preferred mixtures are mixtures of at least one alcohol and of water, or of at least one glycol and of water, comprising at least 10% v/v of alcohol or glycol, the remainder being made up of water.

Among these solvent mixtures, a mixture of water and of ethanol in a 50/50 v/v ratio, or a mixture of water and of butylene glycol in a 50/50 v/v ratio, is preferred.

The extraction step per se is preferably carried out by hot reflux for at least 30 minutes.

According to another variant of the invention, the extraction may also be carried out by a method using a polar solvent in the subcritical state, said solvent being advantageously water in the subcritical state.

The extraction may also optionally comprise an additional step comprising treatment of the plant material or of the plant extract, aimed at partially or completely discolouring it, or at purifying it.

This discolouring step may, for example, comprise treatment of the plant material prior to the extraction itself, or of the extract, with a solution of an apolar solvent or of a mixture of apolar solvents, preferably treatment with a $C_6$-$C_7$ alkane, for example heptane, or treatment comprising bringing the extract into contact with particles of active carbon, or alternatively treatment with $CO_2$ in the supercritical state.

The extraction may be completed by a step of partial or total elimination of the extraction solvents.

In the first case, the extract is generally concentrated until an aqueous concentrate devoid of significant amounts of organic solvent is obtained; in the second case, a dry residue is obtained.

Alternatively, the product of the extraction step may be lyophilized or atomized so as to be in the form of a powder.

The powder may be used as it is in a cosmetic composition according to the invention, or may be redispersed in a solvent or solvent mixture.

In general, the product of the extraction step may be dissolved or dispersed in a solvent or solvent mixture, so as to be used as an active agent in the cosmetic compositions of the invention.

The solvent or the solvent mixture in which the extract is dissolved or dispersed may be identical to or different from that having been used for the extraction.

The extract of the invention may also be adsorbed on to a support advantageously chosen from porous or nonporous nylon powders and micas or any lamellar mineral substance.

In this case, the extract used is preferably an aqueous extract.

A further aspect of the invention is the use of a plant extract of a plant of the species belonging to the *Lepechinia* genus, preferably an extract of the plant species *Lepechinia caulescens*, as a cosmetically active agent in cosmetic compositions.

The invention concerns in particular the use of the extract in a cosmetic composition, as one of the cosmetic agents or as one of the active agents for carrying out the types of cosmetic care mentioned above, especially for preventing or delaying the appearance of the signs of skin ageing or slowing down the effects thereof; and/or for reconstructing the epidermis or the stratum corneum thereof, which is damaged, in particular by ultraviolet radiation, and/or for preventing or slowing down hair loss, for accelerating or promoting hair regrowth, in particular in the case of alopecia, or for reinforcing brittle hair, and/or for promoting growth of the nail and/or reinforcing the strength thereof.

According to the invention, the cosmetic agent, or the active agent mentioned above, is more particularly delivered topically in the form of a cosmetic composition containing it as one of its active agents, in particular in solution or in dispersion in at least one cosmetically acceptable carrier suitable for application of said composition to the skin of the body or of the face, to the scalp, or to the nails.

Thus, the cosmetic composition comprises an effective amount of at least one cosmetic agent as defined above comprising an extract of the plant *Lepechinia*, for obtaining the desired effect.

Another aspect of the invention is a cosmetic care method for preventing or delaying the appearance of the signs of skin ageing or reducing the effects thereof, said method being characterized in that it comprises the delivery, to at least one area concerned of the skin of the body or of the face, of an effective amount of at least one cosmetically acceptable agent that activates or stimulates survivin expression, comprising at least one extract of the plant of the *Lepechinia* genus, as defined above or as resulting from the examples, in particular a plant of the species *Lepechinia caulescens*.

According to a first embodiment of the invention, said cosmetic care method comprises the application, to at least one part of the skin of the face or of the body displaying or liable to display signs of skin ageing, of a cosmetic composition, for example a cream or a serum, comprising, as one of its active agents, at least one active agent that stimulates survivin expression, comprising at least one extract of a plant belonging to the *Lepechinia* genus, in particular of the species *Lepechinia caulescens*, for the purpose of obtaining an anti-wrinkle effect, through a phenomenon of cellular re-densifying of the epidermis, and in the hollow of the wrinkles, and through the acceleration or the maintenance of the renewal thereof. It is known that the phenomenon of cellular re-densifying of the epidermis becomes finer with age, while the cell renewal of the epidermis decreases with age.

According to another embodiment of the invention, said cosmetic care method comprises the application of a composition comprising, as one of its active agents, at least one extract that activates or stimulates survivin expression, comprising at least one extract of a plant belonging to the *Lepechinia* genus, in particular of the species *Lepechinia caulescens*, to areas of the skin exposed to sunlight, in order to reinforce the resistance of the keratinocytes of the basal layer of the epidermis to apoptosis in such a way as to reduce the cell loss which results therefrom at the basal layer and to thus limit photoageing. It is known that apoptosis is induced by the UVB rays of solar radiation.

Yet another aspect of the invention relates to a cosmetic or dermatological care method for reconstructing the epidermis or the stratum corneum thereof when it is damaged, in particular by ultraviolet radiation, for the purpose of accelerating or promoting healing. This method comprises the delivery, to the area of the skin, of the body or of the face concerned, of an effective amount of at least one cosmetically acceptable agent that stimulates survivin expression in the skin, and that contains an extract of the plant of the genus *Lepechinia*, in particular a plant of the species *Lepechinia caulescens*.

Yet another aspect of the invention relates to a cosmetic care method aimed at restoring the functioning of the hair cycle, for preventing or slowing down hair loss, for promoting or accelerating hair regrowth, in particular in the case of alopecia, or for reinforcing brittle hair, the growth of the hair shaft resulting from multiplication of the keratinocytes of the hair bulb, characterized in that it comprises the delivery, to at least one part of the scalp, of an effective amount of at least one cosmetically acceptable agent that activates or stimulates survivin expression in the scalp, comprising an extract of the plant of the *Lepechinia* genus, in particular a plant of the species *Lepechinia caulescens*.

Yet another aspect of the invention relates to a cosmetic care method for promoting growth of the nails and/or reinforcing the strength thereof, characterized in that it comprises the delivery, to the nail or at least a part of the surrounding area, of an effective amount of at least one cosmetically acceptable agent that activates or stimulates survivin expression so as to promote said growth of the nail and/or to reinforce the strength thereof, comprising at least one plant extract of a plant of the *Lepechinia* genus, in particular a plant of the species *Lepechinia caulescens*.

The tests carried out by the inventors have shown that the unexpected properties of the extract of the invention can also be obtained or improved in cosmetic compositions in which the extract is combined with other active agents having cosmetic effects similar and/or complementary to the extract of the invention.

In particular, the *Lepechinia* extract may be used in combination with at least one other active agent which contributes to the maintenance and to the integrity of the structure of the skin.

According to a first embodiment, the composition comprising the extract according to the invention may also contain at least one other active agent, in particular that activates or stimulates survivin expression in the skin, said agent possibly being an isolated molecule or the product of an extraction method, and being advantageously chosen from forskolin or an extract containing it, such as an extract of *Coleus forskolii*, or else an extract of a plant of the *Limnophila* genus, in particular of the plant species *Limnophila conferta*, or belonging to one of the plant species among *Nostoc commune, Scenedesmus dimorphus, Curcuma longa, Crocus sativus* and *Daniellia oliveri*.

The effectiveness of a cosmetic active agent according to the invention will be advantageously improved by molecules or extracts that stimulate the expression of the adhesion proteins, such as beta-1 integrins, of epidermal keratinocytes, and the adhesion itself of these cells (magnesium aspartate, manganese salts and derivatives, certain peptides recognized by the integrin, such as the arginine-glycine-aspartic acid sequence, certain growth factors such as KGF).

The activating effectiveness of a cosmetic active agent according to the invention may also be advantageously improved by means of molecules or extracts capable of inhibiting phosphodiesterases which degrade cAMP, such as methylxanthines, and in particular caffeine, and which result in an increase in the intracellular cyclic AMP level.

The compositions comprising a cosmetic agent as described above may also comprise one or more other active agents that may be chosen from substances having a skin-lightening activity; substances having a slimming activity; substances having a hydrating activity; substances having a calming, soothing or relaxing activity; substances having an activity that stimulates the microcirculation of the skin so as to improve the radiance of the complexion, in particular of the face; substances having a sebum-regulating activity for the care of greasy skin; substances for cleansing or purifying the skin; substances having a free-radical-scavenging activity; substances for reducing or delaying the effects of skin ageing, in particular the formation of wrinkles, through an activity aimed at promoting maintenance of the skin structure and/or at limiting degradation of the extracellular matrix of the superficial layers of the dermis and of the epidermis and/or at obtaining a skin-protecting, correcting or restructuring effect; substances having an anti-inflammatory activity.

In addition to the extract of the invention, said cosmetic composition comprises at least one cosmetically acceptable excipient which may be chosen from pigments, dyes, polymers, surfactants, rheology agents, fragrances, electrolytes, pH modifiers, antioxidants and preservatives, and mixtures thereof.

The cosmetic composition according to the invention may, for example, be a serum, a lotion, an emulsion, for example a cream, or else a hydrogel, preferably a mask, or may be in the form of a stick, of a patch, or else of a hygiene product for the scalp, such as a shampoo or a conditioner, or else a make-up product, in particular a composition intended to be applied to the nails, for example a nail varnish.

The process conditions for obtaining the *Lepechinia* plant extract, in particular an extract of the species *Lepechinia caulescens*, may be the same as those described above or in Example 1 or 2.

According to one particular embodiment, the invention concerns a cosmetic composition containing at least one extract according to the invention as defined above, alone or in combination with other extracts, in solution or in dispersion in a cosmetically acceptable carrier compatible with topical application to the skin or the nails.

According to another preferred variant of one of the abovementioned care methods, the cosmetically acceptable agent also comprises forskolin or an extract containing it.

According to any one of the abovementioned subjects of the invention, the agent according to the invention may be delivered topically in the form of a cosmetic composition comprising said agent as one of its active agents, said composition also comprising at least one cosmetically acceptable excipient, by application of this composition to the part of the body concerned.

Finally, another aspect of the invention relates to a method for the in vitro culture of stem cells and/or of cells with a high clonogenic potential for the purposes of fundamental studies or for the purposes of the production of cultured epidermis, such as reconstructed epidermis, for therapeutic purposes, such as for example, in the case of a graft, following burns or ulcerative wounds which heal poorly, characterized in that it comprises the addition, to a culture medium, of an active agent comprising at least one extract of a plant of the *Lepechinia* genus, in particular a plant of the species *Lepechinia caulescens*, in an effective amount for maintaining said cells in culture or for the production of epidermis.

According to one variant, the concentration of active agent or of extract is between 0.001% and 5%, in particular between 0.01% and 3% by weight of the culture medium.

In addition, for any aspect of the invention, the term "effective amount" is intended to mean an amount which is at least equal to the amount necessary:

a) for preventing or delaying the appearance of the signs of skin ageing or slowing down the effects thereof, b) for reconstructing the epidermis or the stratum corneum thereof, which is damaged, in particular by ultraviolet radiation, and/or c) for restoring the functioning of the hair cycle, in order to prevent or slow down hair loss, to accelerate or promote hair regrowth, in particular in the case of alopecia, or to reinforce brittle hair, and/or d) for promoting growth of the nail and/or reinforcing the strength thereof, and/or e) for maintaining stem cells, and/or cells with a high clonogenic potential, in culture in order to make it possible to conserve these cultures for a period of time sufficient to carry out the culturing under good conditions, and also to carry out the production of epidermis, when necessary.

In practice, this effective amount can be readily determined by those skilled in the art. In general, the concentration of agent comprising an extract of *Lepechinia*, or of extract on its own, will be between 0.001% and 5% by weight, in particular between 0.01 and 3% by weight, of the composition or of the culture medium.

As regards the extract, for any aspect, the concentration will be expressed in weight of dry extracts relative to the weight of the composition or of the culture medium.

As demonstrated by specific tests which have been carried out and reported in Examples 1 and 2, the cosmetic agent according to the invention is effective in particular by stimulating, unexpectedly, the expression of survivin in the stem cells of the basal layer of the dermis or of the epidermis.

Other objectives, characteristics and advantages of the invention will emerge clearly from the explanatory description which follows and which is given in reference to several exemplary embodiments of the invention, given simply by way of illustration and which could not in any way limit the scope of the invention. In the examples, the temperature is in degrees Celsius, the pressure is atmospheric pressure, and the amounts or the percentages are given by weight, unless otherwise indicated.

EXAMPLES

Materials And Methods

1) Cell Culture

The normal human keratinocytes are cultured in 75 cm$^2$ flasks, in an incubator at 37° C. under a humid atmosphere containing 5% $CO_2$, in serum-free keratinocyte medium supplemented with EGF (Epidermal Growth Factor) and with BPE (Bovine Pituitary Extract) (KSFMc) (Gibco ref: 17005-034+37000-015). The cells are seeded (day D0) into 48-well microplates in a proportion of 50 000 cells in 500 μl of medium per well.

After incubating for 24 hours (day D1), the cells have become adherent and the treatment step is then carried out. The seeding medium is removed and the treatment medium, each containing an extract to be evaluated in solution in a solvent (for example, DMSO) at the various concentrations, is then added to each culture well. A control is also prepared using this same solvent and in the same proportions.

A peak of survivin expression by the cells is observed after treatment for 16 hours. The wells are then rinsed with PBS. Half the wells of the microplate are used to lyse the keratinocytes and to assay the intracellular survivin. The other half of the wells of the microplate are used to assay the total proteins by the BCA method, which makes it possible to relate the amount of survivin assayed back to a unit amount of protein.

A phase of measuring the cytotoxicity of each plant extract tested is necessary beforehand, in order to be able to subsequently evaluate the effect of the extract at noncytotoxic doses.

To this end, the cytotoxic dose of the extract is determined by means of the XTT test (ref: Cell Proliferation Kit II, Roche Diagnostic). The tetrazolium salt (XTT reagent) is converted to formazan by the dehydrogenases located in the mitochondrial respiratory chain. Only the living cells, the respiratory chain of which is functional, are capable of producing formazan, an orange compound detected at 450 nm.

Each extract tested is diluted in order to prepare a doubling dilution range on a microplate, the concentration of extract of the test samples ranging from 50 mg/ml to 0.195 mg/ml. Each pre-prepared dilution is finally diluted to $1/1000$th in the KSFM-C medium and is then brought into contact with the keratinocytes for 48 h, at which point the cytotoxicity test will be carried out.

2) Assaying Survivin

The activity of plant extracts of plants of the plant species *Lepechinia caulescens* with respect to survivin expression is evaluated. The survivin is assayed by means of an ELISA enzymatic immunoassay (ref: Duoset Survivin ELISA from R&D Systems) on cultures of normal human keratinocytes.

The total proteins are assayed by means of a BCA colorimetric test (reference: BC Assay Kit, Uptima Interchim), by measuring absorbance at 570 nm.

For the ELISA assay of survivin after treatment for 16 h, the wells are rinsed with PBS and then 100 μl/well of lysis buffer are added, followed by incubation for 10 minutes with gentle agitation. This buffer contains antiproteases, which prevent degradation of the proteins, including the survivin, during the cell lysis.

The ELISA microplate (reference Clear Microplate R&D systems DY992) is prepared. A standard range with human survivin is prepared from 0 to 2000 pg/ml under the same conditions as with the cell lysates. After the enzyme reaction has been blocked with sulphuric acid, the survivin is quantified by measuring the absorbance at 450 nm.

Example 1

Preparation of an Extract of *Lepechinia caulescens* Leaves and Determination of the Activity Thereof With Respect to Survivin Expression The plant material, formed from leaves of *Lepechinia caulescens* in the dry state, is ground extemporaneously using a laboratory mill-mixer, to an average particle size of the order of 0.1 to 1 mm.

10 g of ground plant material are introduced into a 250 ml round-bottomed flask, into which 150 ml of a solvent or solvent mixture, among those listed below, are added:

water,
butanol,
90/10 (v/v) ethanol/water,
propanol,
50/50 (v/v) ethanol/water,
50/50 (v/v) butylene glycol/water.

The round-bottomed flask surmounted by a bulb condenser is stirred magnetically in a thermostated bath, and then heated to the solvent reflux.

The reflux is maintained for 30 minutes with stirring.

Once the heating has stopped, the round-bottomed flask is allowed to cool to ambient temperature outside the bath.

The mixture is then vacuum-filtered through a üichner funnel with a Whatman 70 μm GF/F filter and a tared flask; the filtrate 1 is thus obtained. The cake is washed on the Büichner funnel with 50 ml of extraction solvent; the filtrate 2 is obtained.

The two filtrates were combined and weighed.

The resulting filtrate is introduced into a pre-tared round-bottomed flask, and then concentrated to dryness on a rotary evaporator under vacuum in a water bath at a maximum temperature of 50° C.

The dry residue is quantified in order to obtain the extraction yield by mass, expressed as mass of dry extract obtained per 100 g of starting plant material in the dry ground state.

The extraction yields by mass, obtained for each method implemented with a solvent or solvent mixture among those listed above, are indicated in Table I below:

TABLE I

| Extraction solvent | Ratio (v/v) | Yield by mass (%) |
| --- | --- | --- |
| Water | 100 | 28% |
| Ethanol/water | 50/50 | 29% |
| Ethanol/water | 90/10 | 21% |
| Ethanol | 100 | 10% |
| Butanol | 100 | 12% |
| Butylene glycol/water | 50/50 | 24% |

Example 2

Activity of Extracts of *Lepechinia caulescens* With Respect to Survivin Expression The dry extracts prepared in Example 1 are each diluted to the concentration of 3.125 mg/ml in DMSO.

During the treatment on cells, each extract is added to the culture medium in order to obtain a final concentration of 0.1 % v/v, i.e. 3.125 µg/ml. A solvent control (DMSO) is also prepared, with the final concentration of 0.1% v/v.

Table II below indicates the activity of each the extracts of *Lepechinia caulescens* leaves tested with respect to survivin, relative to the basal level of expression, represented by the solvent control, which constitutes 100%.

TABLE II

| Extraction solvent | % activation |
| --- | --- |
| 100% water | 0 |
| 50/50 ethanol/water | +37% |
| 90/10 ethanol/water | +30% |
| Ethanol | +6% |
| Butanol | +15% |
| 50/50 BG/water | +23% |

Conclusion: except for the aqueous extract, all the extracts significantly increase intrakeratinocyte survivin expression, compared to the basal level of protein expression (controls). The extracts obtained from a mixture of water and an alcoholic or glycolic polar solvent are those which most strongly stimulate survivin expression by keratinocytes.

Example 3

Cosmetic Composition Comprising an Extract of *Lepechinia caulescens* Leaves

The dry extract obtained after extraction with an ethanol/water (50/50 v/v) solvent mixture is solubilized at 1% by mass in an ethanol/water mixture.

A solution at 1% by mass of dry extract is obtained, and is used in the cosmetic composition below:

| Plant extract of *Lepechinia caulescens* | 0.1% |
| --- | --- |
| Surfactant (Arlacel ® 165 VP) | 5% |
| 95% cetyl alcohol | 1% |
| Stearyl alcohol | 1% |
| Beeswax | 1.5% |
| Oil (Perleam ®) | 8.5% |
| Tri caprate/caprylate glycerides | 3% |
| Silicone oil (dimethicone 100 CS) | 1% |
| Polymer (Keltrol ®) | 0.35% |
| Sodium hydroxide | 0.04% |
| Tetrasodium EDTA powder | 0.1% |
| Preservatives | 0.5% |
| Water | qs 100 |

The cosmetic composition is prepared in the usual manner, well known to those skilled in the art, by mixing the various components in one or more steps.

This composition can be applied to the skin or the scalp or else the nails daily for several weeks in order to obtain the abovementioned cosmetic effects.

Example 4

Antiwrinkle Tonic Lotion Comprising an Extract of *Lepechinia caulescens*

The dry extract obtained after extraction with an ethanol/water (50/50 v/v) solvent mixture is solubilized at 1% by mass in an ethanol/water mixture.

A solution at 1% by mass of dry extract is obtained, and is used in the cosmetic composition below:

| Plant extract of *Lepechinia caulescens* | 2% |
| --- | --- |
| Butylene glycol | 3% |
| EDTA | 0.1% |
| Solubilizing agent | 1% |
| Fragrance concentrate | 0.3% |
| Ethanol | 5% |
| UV screen (benzophenone-4) | 0.13% |
| Water | qs 100 |

The cosmetic composition is prepared in the usual manner, well known to those skilled in the art, by mixing the various components in one or more steps.

This composition can be applied daily to the areas of the skin comprising wrinkles, for several weeks, in order to obtain an effect of reduction or of complete disappearance of said wrinkles.

Example 5

Antiwrinkle Day Cream in the Form of an Emulsion Comprising an Extract of *Lepechinia caulescens*

The dry extract obtained after extraction with an ethanol/water (50/50 v/v) solvent mixture is solubilized at 1% by mass in an ethanol/water mixture.

A solution at 1% by mass of dry extract is obtained, and is used in the cosmetic composition below:

| Plant extract of *Lepechinia caulescens* | 2% |
| --- | --- |
| Steareth-21 (Brij 721) | 2.5% |
| Glyceryl stearate (Tegrin) | 1.1% |
| Stearyl alcohol | 5% |

-continued

| | |
|---|---|
| Glycerol tri caprate/caprylate | 12.5% |
| Butylene glycol | 3% |
| Glycerol | 2% |
| Preservative | 0.5% |
| Fragrance concentrate | 0.5% |
| UV screen (octyl methoxycinnamate) | 7.5% |
| Water | qs 100 |

The cosmetic composition is prepared in the usual manner, well known to those skilled in the art, by mixing the various components in one or more steps.

This composition can be applied daily to the areas of the skin comprising wrinkles, for several weeks, in order to obtain an effect of reduction or of complete disappearance of said wrinkles.

What is claimed:

1. A cosmetic composition comprising:
   at least one cosmetic agent comprising at least one plant extract of the species *Lepechinia caulescens* at a concentration of between 0.001% and 5% by dry weight of extract relative to the weight of the composition,
   said extract is obtained by a method comprising bringing the plant into contact with a polar solvent that is a C2-C4 alcohol or a mixture of a C2-C4 alcohol and water, said extract being admixed with a cosmetically acceptable carrier; and
   wherein the cosmetic composition is in the form of a lotion, an emulsion, a cream, or a hydrogel.

2. The composition according to claim 1, wherein said extract is an extract of the whole plant.

3. The composition according to claim 1, wherein said extract is an extract of a part of said plant, said part selected from the root, the rhizome, the leaves, the flowers, the seeds, the floral buds, and any mixture thereof.

4. The composition according to claim 1, wherein the extract is obtained from the above-ground parts of the plant.

5. The composition according to claim 4, wherein the extract is obtained from the leaves of the plant.

6. The composition according to claim 1, wherein said polar solvent is a mixture of at least one $C_2$-$C_4$ alcohol and water, the mixture comprising at least 10% v/v of the $C_2$-$C_4$ alcohol, the remainder being made up of water.

7. The composition according to claim 1, wherein said extract is absorbed on to a support selected from porous or nonporous nylon powders, micas, or a lamellar mineral substance.

8. The composition according to claim 1, further comprising at least one other active agent which contributes to the maintenance and the integrity of the skin structure.

9. The composition according to claim 1, wherein the extract is present in said composition at a concentration of between 0.01% and 3% by dry weight of extract relative to the weight of the composition.

10. The composition according to claim 1, wherein the cosmetic composition is in the form of an emulsion or a hydrogel.

11. The cosmetic composition of claim 1, wherein the cosmetically acceptable carrier comprises a pigment, a dye, a polymer, a surfactant, a rheology agent, a fragrance, an electrolyte, a pH modifier, or a mixture thereof.

12. The cosmetic composition of claim 1, wherein the cosmetically acceptable carrier comprises a pigment, a dye, or a fragrance.

13. The composition of claim 1, wherein the cosmetic composition is in the form of a lotion or a cream.

14. The composition of claim 13, wherein the cream is a shampoo.

15. The composition of claim 1, in the form of a lotion.

16. The composition of claim 1, in the form of a cream.

17. A cosmetic composition comprising
   at least one cosmetic agent comprising at least one plant extract of the species *Lepechinia caulescens* at a concentration of between 0.001% and 5% by dry weight of extract relative to the weight of the composition,
   said extract is obtained by a method comprising bringing the plant into contact with a polar solvent that is a C2-C4 alcohol or a mixture of a C2-C4 alcohol and water, said extract being admixed with a cosmetically acceptable carrier;
   wherein said C2-C4 alcohol is ethanol, butanol, a glycol, or a mixture thereof; and
   wherein the cosmetic composition is in the form of a lotion, an emulsion, a cream, or a hydrogel.

18. The composition according to claim 17, wherein said glycol is glycerol, butylene glycol, propylene glycol, or a mixture thereof 19. The composition according to claim 17, wherein the extract is present in said composition at a concentration of between 0.01% and 3% by dry weight of extract relative to the weight of the composition.

20. The composition of claim 17, wherein the cosmetic composition is in the form of an emulsion or a hydrogel.

21. The cosmetic composition of claim 17, wherein the cosmetically acceptable carrier comprises a pigment, a dye, a polymer, a surfactant, a rheology agent, a fragrance, an electrolyte, a pH modifier, or a mixture thereof.

22. The cosmetic composition of claim 17, wherein the cosmetically acceptable carrier comprises a pigment, a dye, or a fragrance.

23. The composition of claim 17, wherein the cosmetic composition is in the form of a lotion or a cream.

24. The composition of claim 23, wherein the cream is a shampoo.

25. The composition of claim 17, in the form of a lotion.

26. The composition of claim 17, in the form of a cream.

27. A cosmetic composition comprising
   at least one cosmetic agent comprising at least one plant extract of the species *Lepechinia caulescens* at a concentration of between 0.001% and 5% by dry weight of extract relative to the weight of the composition,
   said extract is obtained by a method comprising bringing the plant into contact with a polar solvent mixture comprising a mixture of water and ethanol in a 50/50 v/v ratio, or a mixture of water and of butylene glycol in a 50/50 v/v ratio,
   said extract being admixed with a cosmetically acceptable carrier; and
   wherein the cosmetic composition is in the form of a lotion, an emulsion, a cream, or a hydrogel.

28. The composition according to claim 27, wherein the extract is in the form of a powder prepared by lyophilization or atomization of said extract.

29. The composition according to claim 27, wherein the extract is present in said composition at a concentration of between 0.01% and 3% by dry weight of extract relative to the weight of the composition.

30. The cosmetic composition of claim 27, wherein the cosmetically acceptable carrier comprises a pigment, a dye, a polymer, a surfactant, a rheology agent, a fragrance, an electrolyte, a pH modifier, or a mixture thereof.

31. The cosmetic composition of claim 27, wherein the cosmetically acceptable carrier comprises a pigment, a dye, or a fragrance.

32. The cosmetic composition of claim 27, in the form an emulsion or a hydrogel.

33. The cosmetic composition of claim 27, in the form of a lotion or a cream.

34. The composition of claim 33, wherein the cream is a shampoo.

35. The composition of claim 27, in the form of a lotion.

36. The composition of claim 27, in the form of a cream.

* * * * *